United States Patent
Mainz et al.

(10) Patent No.: US 6,552,238 B1
(45) Date of Patent: Apr. 22, 2003

(54) SEPARATION OF HEAVY ENDS FROM STREAMS OF HALOGENATED ALKANES

(75) Inventors: Eric L. Mainz, Goddard, KS (US); Richard L. Wilson, Mulvane, KS (US)

(73) Assignee: Vulcan Chemicals, Birmingham, AL (US)

(*) Notice: Subject to any disclaimer, the term of this patent is extended or adjusted under 35 U.S.C. 154(b) by 0 days.

(21) Appl. No.: 09/942,914

(22) Filed: Aug. 31, 2001

(51) Int. Cl.⁷ .................................. C07C 17/38
(52) U.S. Cl. .................. 570/177; 570/178; 570/262; 570/263
(58) Field of Search ................ 570/177, 178, 570/262, 263

(56) References Cited

U.S. PATENT DOCUMENTS 5,843,286 A * 12/1998 Roth et al.
6,229,059 B1 * 5/2001 Motz

* cited by examiner

*Primary Examiner*—Alan Siegel
(74) *Attorney, Agent, or Firm*—Burns, Doane, Swecker & Mathis, LLP

(57) ABSTRACT

Provided is a method and system for separating heavy ends from a halogenated alkane in a waste stream. The method includes: (a) removing a bottom fraction containing heavy ends from a catalyst recovery unit and conveying the bottom fraction to a vessel; (b) introducing steam into the bottom fraction containing heavy ends; (c) removing a halogenated alkane vapor and a water vapor from the waste treatment unit; (d) condensing the halogenated alkane and water vapors; and (e) separating the halogenated alkane phase and water phase from the heavy ends.

15 Claims, 3 Drawing Sheets

SEPARATION OF HEAVY ENDS FROM STREAMS OF HALOGENATED ALKANES

BACKGROUND OF THE INVENTION

1. Field of the Invention

The invention relates to methods and systems for the separation of halogenated alkane streams from heavy ends. In particular, the invention is directed to the separation of 1,1,1,3,3-pentachloropropane from the heavy ends produced in the formation of 1,1,1,3,3-pentachloropropane.

2. Description of the Related Art

Fluorocarbon producers have actively pursued the production of fluorocarbons to replace the banned chlorofluorocarbons (CFC's). These fluorocarbons will require hydrochlorocarbon feedstocks.

Several fluorochemical producers have targeted fluorocarbon 1,1,1,3,3-pentafluoropropane, utilizing 1,1,1,3,3-pentachloropropane as the feedstock, as the primary replacement product for foam blowing Zil'bennan et al. ("Synthesis of liquid telomers of vinyl chloride with carbon tetrachloride," *J. Org. Chem.* USSR (English Transl.), 3:2101–2105, 1967) prepared 1,1,1,3,3-pentachloropropane in a 58% yield by the reaction of carbon tetrachloride ($CCl_4$) and vinyl chloride using ferrous chloride tetrahydrate in isopropanol. In addition, Kotora et.al. ("Addition of tetrachloromethane to halogenated ethenes catalyzed by transition metal complexes," *J Mol. Catal.*, 77(1):51–60, 1992) prepared 1,1,1,3,3-pentachloropropane in high yields using either cuprous chloride/butylamine or tris(triphenylphosphine)dichlororuthenium.

European Patent Application No. 131561 describes a very general process for the addition of a haloalkane compound to an alkene or alkyne compound in the presence of iron metal and a phosphorus (V) compound to form halogenated alkanes. EP 131561 sets forth several examples of the batch reaction of ethylene and carbon tetrachloride to produce 1,1,1,3-tetrachloropropane. EP 131561 also mentions a wide variety of other olefins and alkynes, including vinyl halides. It states that the batch process could be made continuous, but does not include any specific information concerning how this would be carried out.

U.S. Pat. No. 6,187,978 describes a process based on Kharasch chemistry where polyhalogenated alkanes and olefins are reacted in the presence of a transition metal catalyst. The reaction results in the following Kharasch reaction:

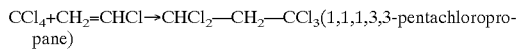
$CCl_4 + CH_2=CHCl \rightarrow CHCl_2-CH_2-CCl_3$ (1,1,1,3,3-pentachloropropane)

U.S. patent application Ser. No. 09/671,993 filed Sep. 29, 2000 now allowed, describes a process which includes a reaction step, a catalyst recovery step, and a process to purify the haloalkane product. In the process, a portion of the catalyst stream is withdrawn from the catalyst recovery unit and is disposed of as a waste stream in order to prevent the build up of unreactive by-products. The waste stream can contain up to 50 weight percent of 1,1,1,3,3-pentachloropentane product. Thus, the volume of product in the waste stream constitutes a significant loss of feed conversion to the desired product.

Conventional distillation and even low temperature distillation of waste streams has resulted in decomposition of both the 1,1,1,3,3-pentachloropropane product and catalyst components in the waste stream. Tar-like by-products, which foul the equipment, for example, are formed. Likewise, treatment of waste streams by performing a combination of solvent and aqueous extraction is ineffective and costly. Generally, a primary aqueous extraction is followed by the addition of non-polar solvents to separate the waste stream into two phases. These phases can then be further separated to recover the reactants. However, tests have demonstrated that extractions through the employment of aqueous, or aqueous plus inorganic salts and/or acids, or aqueous plus polar solvents, were ineffective in extracting iron, useful reactants and products. Aqueous based extractions induce precipitation of solids, which in turn require increased waste handling and waste disposal costs.

To meet the requirements of the fluorocarbon industry of providing a pure fluorocarbon feedstock at a high yield and to overcome the disadvantages of the related art, it is an object of the present invention to provide a novel method for separating heavy ends from a halogenated stream in a facile and cost-effective manner.

It is another object of the invention to recover from the waste stream a halogenated alkane stream, which contains desirable halogenated alkane(s) leaving a heavy ends stream that is disposed of as a waste product. The recovered halogenated alkane stream that can be further purified to give a product for use as a fluorocarbon feedstock.

It is another object of the invention to employ steam in the separation of the heavy ends from the waste stream and to recover the steam as a water phase, which will then be utilized to treat additional waste stream.

BRIEF DESCRIPTION OF THE DRAWINGS

The objects and advantages of the invention will become apparent from the following detailed description of the preferred embodiments thereof in connection with the accompanying drawings, in which.

SUMMARY OF THE INVENTION

Figure 1:
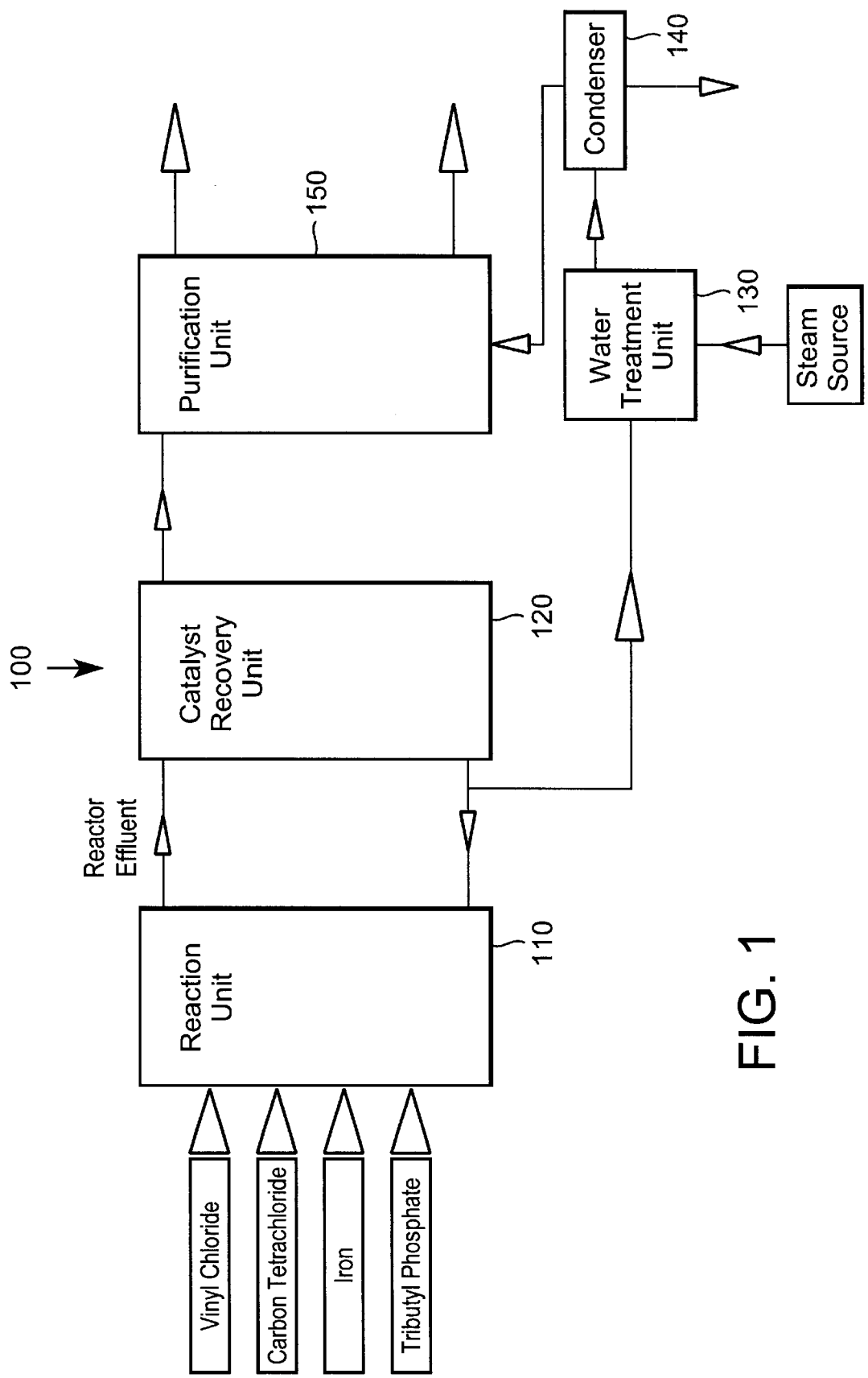
FIG. 1 illustrates a schematic diagram of a system that is used to practice a method for treating a waste stream withdrawn from the catalyst recovery unit to separate the heavy ends from the halogenated alkane.

In accordance with the present invention, an innovative method and system is provided for the separation of heavy ends from a halogenated alkane in a stream of waste removed from the catalyst recovery unit.

In accordance with one aspect of the invention, a method for separating heavy ends from a halogenated alkane in a waste stream is provided. The method includes: (a) removing a bottom fraction containing heavy ends from a catalyst recovery unit and conveying the bottom fraction to a vessel; (b) introducing steam into the bottom fraction containing heavy ends;(c) removing a halogenated alkane vapor and a water vapor from the waste treatment unit; (d) condensing the halogenated alkane and water vapors; and (e) separating the halogenated alkane phase and water phase from the heavy ends.

In accordance with another aspect of the invention a method for the separation of heavy ends from a halogenated alkane stream is provided. The method includes (a) removing a bottom fraction containing heavy ends from a catalyst recovery unit and conveying the bottom fraction to a vessel; (b) maintaining the temperature of the vessel above the boiling point of water and at a predetermined pressure; (c) introducing water into the vessel where a portion of the water is converted into steam and is mixed with the heavy ends and all or a portion of the water is converted into steam and mixes with the waste stream to form a vapor mixture containing steam and the haloalkane fraction of the waste stream; (d) condensing the haloalkane mixture and the steam; (e) separating a halogenated alkane phase from the water phase; and (f) periodically or continuously purging a portion of liquid in the bottom of the vessel.

In accordance with another aspect of the invention, a system for separating heavy ends from a halogenated alkane stream is provided. The system includes (a) a waste treatment unit for receiving a bottom fraction containing heavy ends from a catalyst recovery unit; (b) a water source for providing water to the waste treatment unit, where a portion of the water is converted into steam and is mixed with the heavy ends to form a water and halogenated alkane vapor; (c) a condenser for condensing the haloalkane and water vapor mixture; and (d) separating the halogenated alkane phase from the water phase.

DETAILED DESCRIPTION OF THE PREFERRED EMBODIMENTS OF THE INVENTION

The invention will now be described with reference to exemplary embodiments thereof. A first aspect of the invention relates to a method for the efficient removal/separation of a haloalkane product from a mixture of catalyst, solvent, metal particles, metal chlorides and high boiling chlorinated by-products formed in a Kharasch chemistry type process.

The separation method of the present invention can be applied to any haloalkane product manufactured based on Kharasch chemistry. In a preferred process, a catalyst mixture is employed to manufacture 1,1,1,3,3-pentachloropropane by the addition reaction of carbon tetrachloride and vinyl chloride. Particularly, the catalyst mixture includes tributyl phosphate (TBP), metallic iron, ferrous chloride and ferric chloride. A system and method for the manufacture of 1,1,1,3,3-pentachloropropane based on the above-described reaction is disclosed in U.S. patent application Ser. No. 09/671,993 filed Sep. 29, 2000 now allowed, and is hereby incorporated by reference in its entirety.

The preferred embodiments are discussed below with reference to the FIGS. where the same reference numbers denote like features. In accordance with a preferred embodiment, and as illustrated in FIG. 1, the system includes a reaction chamber 110, a catalyst recovery unit 120, a purification unit 150 and a waste treatment 130. The reaction components (i.e., vinyl chloride, carbon tetrachloride, tributyl phosphate (TBP), and iron) are continuously fed into reactor unit 110.

Reactor unit 110 is agitated to mix the reactor feed and keep the iron powder suspended. Powdered iron is consumed in reactor 110, producing ferrous chloride and ferric chloride. These components (i.e., ferrous chloride and ferric chloride) and TBP form complexes miscible in reactor contents. These complexes are catalytic and promote the Kharasch reaction. Side reactions produce chlorinated hydrocarbon by-products. The major by-products are two hexachloropentane isomers (e.g., 1,1,1,3,5,5-hexachloropentane and 1,1,3,3,5,5-hexachloropentane).

Reactor contents are continually withdrawn from the reactor and routed to the catalyst recovery unit 120. The catalyst recovery unit 120 distills the reactor effluent into distillate and a bottom fraction. The distillate fraction, containing unconverted carbon tetrachloride, unconverted vinyl chloride, 1,1,1,3,3-pentachloropropane, trace light by-products and trace heavy by-products, is routed to purification unit 150 to further purify the 1,1,1,3,3-pentachloropropane product.

The bottom fraction contains ferric chloride, TBP, 1,1,1,3,5,5-hexachloropentane, 1,1,3,3,5,5-hexachloropentane, high boiling point components hereinafter referred to collectively as heavy ends) and 1,1,1,3,3-pentachloropropane (hereinafter, referred to as halogenated alkane). Substantially all catalyst components remain in the heavy ends. The bottom fraction is continuously drawn from the catalyst recovery unit 120 in two streams. One stream is recycled back to the reactor, where ferric chloride and TBP content resume the roles of catalyst components. The second stream (hereafter referred to as the waste stream) that would normally be routed to waste is further processed to separate the heavy ends from the halogenated alkane. The waste treatment unit 130 receiving the waste stream is a vessel made of corrosion resistant materials. Nickel alloys, polytetrafluoroethylene (PTFE), tantalum, and glass-lined steel, are preferred process wetted materials. Suitable nickel alloys include Nickel 200, Hastelloy™, C-276 and Monel™.

Water vapor in the form of steam is introduced into waste treatment unit 130. A mixture of halogenated alkane and steam are removed from overhead the treatment unit 130 and the mixture is routed to condenser 140. Therein the mixture is condensed (re-liquefied) into a halogenated alkane phase and a water phase. By comparison, the heavy ends remain in waste treatment unit 130. The water and halogenated alkane phases are separated by methods known to those skilled in the art. Subsequently, the halogenated alkane phase is dried. The addition of steam to the heavy ends in the waste stream does not result in significant hydrolysis of the heavy ends nor does it form acidic by-products (e.g., HCl). In fact, the steam effectively stripped the halogenated alkane product from the heavy ends with very little decomposition of the product.

The stripped halogenated alkane product obtained is routed either to the catalyst recovery unit 120 or the purification unit 150 for further purification and thus reclamation of the product component of the waste stream. The water component, on the other hand, can be reintroduced into waste treatment unit 130 in the form of steam to treat a further waste stream.

Figure 2:
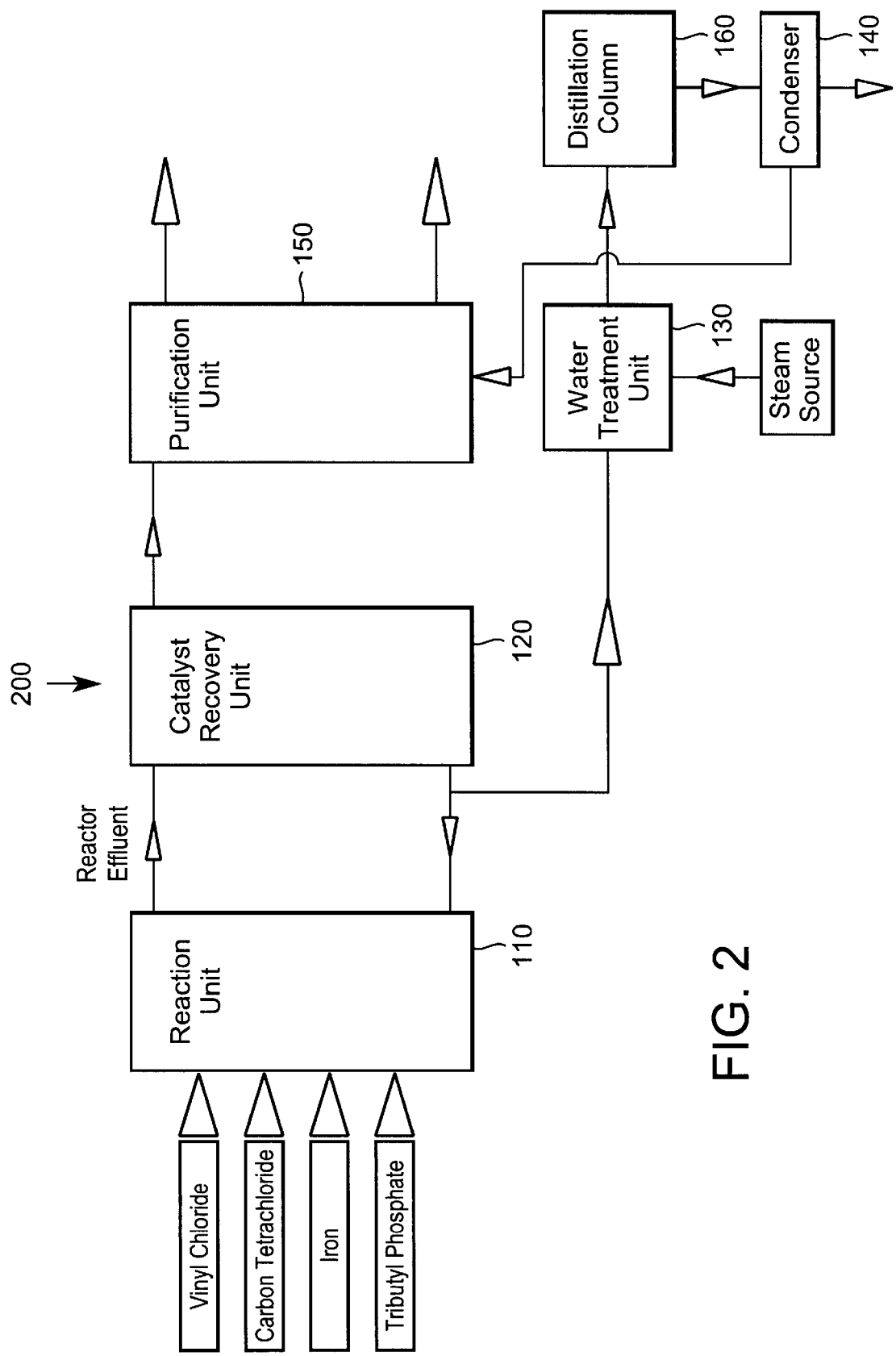
FIG. 2 illustrates a schematic diagram of a system that is used to practice a method for treating a waste stream withdrawn from the catalyst recovery unit to separate the heavy ends from the halogenated alkane through the further employment of a distillation column.

In another preferred embodiment, and as illustrated in FIG. 2, the waste stream is routed from catalyst recovery unit 120 to a waste treatment unit 130 that is maintained at a temperature above the boiling point of water. The temperature of waste treatment unit 130 is dependent on the pressure inside the vessel. Thus, the temperature can be in the range of about 40 to 150° C. and preferably about 80 to 115° C. The pressure can be in a range of about 0.1 to 5.0 atmospheres and preferably 0.5 to 1.5 atmospheres.

A halogenated alkane such as 1,1,1,3,3-pentachloropropane can be separated from the heavy ends based on the proper selection of pressure at which the process is conducted. Conducting the separation process at reduced pressures (i.e., less than ambient) enhances the separation of 1,1,1,3,3-pentachloropropane from isomers such as 1,1,1,3,5,5-hexachloropentane and 1,1,3,3,5,5-hexachloropentane.

In particular, as water is introduced into waste treatment 130, steam is formed and commingled with the waste stream and a portion of the water introduced therein. Steam and halogenated alkane mixture is removed from overhead the treatment unit 130 and the mixture is optionally routed to column 160 where the mixture can be subjected to additional fractionation. The column is preferably packed with structured packing to provide an adequate mass transfer and a low pressure drop, thus enhancing contact between the descending liquid and the rising vapor.

The rising vapor in column 160 contains steam, halogenated alkane and low concentrations of other light components. The vapor is routed to condenser 140, where the mixture is recondensed and separated into a halogenated alkane phase and a water phase, as discussed above. The phase-separated water can be reintroduced into waste treatment unit 130 to treat a further waste stream. However, the phase-separated water can be first treated to remove or neutralize any acidity present. Thus, the water used reduces the volume of waste water produced. On the other hand, as explained above, the halogenated alkane product can be routed to either the catalyst recovery unit 120 or the purification unit 150 for further purification.

In order to further illustrate the methods in accordance with the invention, the following examples are given, it being understood that same are intended only as illustrative and in no way limiting.

COMPARATIVE EXAMPLES

Comparative Example 1

Extraction of Heavy Ends with Water

A pilot plant for the production of HCC240fa (i.e., 1,1,1,3,3-pentachloropropane) had been running under normal conditions for several weeks. A sample of the catalyst recovery unit bottoms material was collected from the HCC240fa pilot plant. A mixture was prepared by mixing 1.8 ml of the bottom fraction with 1.9 ml of deionized water. When shaken, this mixture formed a single immobile phase, yellow in color. No free liquid was present, and the solids adhered to the entire length of the 15-ml centrifuge tube. After centrifuging the mixture for two minutes, there was 1.6 ml of clear yellow liquid under what appeared to be a single creamy yellow colored solid phase amounting to about 2.3 ml.

This upper phase was actually a very thick slurry of solids in the aqueous phase, but there was almost no freely mobile water present. The slurry phase was sticky, quite viscous, and adhered to glass. It is concluded that mixtures of water and bottom fraction from the 1,1,1,3,3-pentachloropropane process are practically intractable.

Comparative Example 2

Extraction of Reactor Effluent with Non-polar Solvents

A sample of reactor effluent from a HCC240fa pilot was used as feedstock. The main component is HCC240fa. This effluent contained much smaller amounts of the by-products 1,1,1,3,5,5-hexachloropentane (HCC-470jfdf) and 1,1,3,3,5,5-hexachloropentane (HCC-470nfaf).

Aliquots of this material were mixed with various non-polar solvents in a 3:5 volume ratio, and then allowed to stand. Thereafter, the mixtures were immersed in ice water for 20 minutes and observed again. The results obtained, and shown below in Table I, indicate that partial separation by this method is possible. When the reactor effluent was cooled to about 0° C. without added solvent there was again a separation of phases, with the lower phase amounting to about 83 vol % of the entire amount. Both phases contained large amounts of iron, tributylphosphate (TBP) and HCC-240fa, but the upper phase contained more of the first two items and less of the latter.

TABLE I

| | Reactor Effluent Phase Separations | | | | | |
|---|---|---|---|---|---|---|
| | Cyclo-pentane | Petroleum ether | Butyl chloride | Carbon tetrachloride | Halocarbon oil | Heptane |
| | | | Room temperature | | | |
| 2-phases | Yes | Yes | No | No | Yes | Yes |
| vol %, bottom | 3 | 6 | — | — | 96 | 4 |
| | | | Ice temperature | | | |
| 2-phases | Yes | Yes | No | Yes | Yes | Yes |
| vol %, bottom | 3 | 6 | — | 96 | 96 | 4 |

Comparative Example 3

Extractions Using Aqueous Solvents Containing Acids or Salts

The sample of reactor effluent described in Comparative Example 2 above, was shaken with various aqueous liquids, including 0.1 Molar (M) HCl, 0.5 M HCl, 1.6 M HCl, 1.9 M $H_2SO_4$, 1.9 M $H_2SO_4$ with 7 M NaCl, 8.5 wt % $H_3PO_4$, 24 wt % $CaCl_2$, 16 wt % $CaCl_2$ with 0.5 M NaCl, 1.0 wt % NaCl, 5 wt % $Na_2SO_3$, 2.5 wt % $(NH_4)H_2PO_4$ with 2.5 wt % $Na_2SO_3$, 5 wt % KBr, 5 wt % $K_2Cr_2O_7$, 5 wt % $NaHSO_3$(pH=5), 5 wt % $NH_4Cl$. In each case, a large amount of solid was formed, so much so that phase separation was severely hindered.

None of these methods provided a good way to commercially separate the iron from the organic layer. In most cases, this is due to the formation of a large amount of solid, which hinders phase separation. The solids appeared to be a mixture of iron compounds with TBP degradation products.

Comparative Example 4

Extractions of Heavy Ends with Aqueous Calcium Chloride and Non-Polar Solvent Perchloroethylene and a catalyst recovery unit bottoms material (See, Table II below) were mixed in a 4:1 weight ratio, and then shaken with aqueous 13 wt % calcium chloride solution and sufficient calcium hydroxide (0.18 grams per gram) to raise the pH of the aqueous phase to 11. A large amount of solids was formed. The mixture was centrifuged, and the organic liquid was decanted. The solids were extracted with perchloroethylene again. After centrifuging and decanting again, the two perchloroethylene extracts were combined and analyzed. Fully 30% of the original TBP and chlorocarbons remained with the solids, presumably in the liquid adsorbed thereupon. Thus, extraction with perchloroethylene, calcium hydroxide, and calcium chloride solution resulted in poor recovery of the chlorocarbons and TBP.

TABLE II

Composition of Bottoms Fraction

| Component | Weight % |
| --- | --- |
| Carbon tetrachloride | 0.1 |
| HCC-240f | 19.5 |
| HCC-470jfdf | 5.8 |
| HCC-470nfaf | 4.7 |
| Iron, total, as $FeCl_3$ | 29.5 |
| Other Organics | 14.0 |
| Phosphorous, total, as TBP | 49.6 |
| TBP, by GC analysis | 26.4 |

Comparative Example 5

Extraction with Hydrochloric Acid and Perchloroethene

Five (5) grams of bottom fraction material was dissolved in 8.06 grams perchloroethene. This mixture was extracted six times with about 2.2 grams of 21.9 wt % hydrochloric acid solution, for a total of 13.27 grams aqueous extract. Very little solids were formed. The organic phase remained black; the combined aqueous phase was bright yellow. All of the original chlorocarbons remained in the perchloroethene solution, as expected. The aqueous phase contained 70% of the total iron from the bottom fraction feed, but only about 1.2% of the total phosphorous.

EXAMPLES OF THE PRESENT INVENTION

Example 1

Steam Stripping of a Bottom Fraction

A sample of bottom fraction was obtained from the R&D HCC240fa pilot plant. The heavy ends material contained about 42 weight percent HCC240fa, 45 percent HCC470jfdf plus HCC470nfaf and the balance being tributylphosphate, iron, phosphorous compounds, polymeric material and traces of low boiling chlorinated hydrocarbon compounds. The heavy ends were subjected to batch steam distillation at ambient pressure, and an average pot liquid temperature of 106° C. The overhead temperature averaged 99° C. The total amount of water fed was 60 grams, for 52 grams of heavy ends feed.

The recovery of the HCC240fa content overhead was 98% of that contained in the feed. The recovery of the HCC470jfdf plus HCC470nfaf content overhead was about 9%. The recovered steam distillation bottoms contained virtually all of the tributylphosphate and 91% of the total HCC470jfdf plus HCC470nfaf fed. There was no evidence of decomposition.

Example 2

Steam Stripping of a Bottom Fraction

Lab distilling equipment was set up with a pump to feed liquid water at a constant rate, using a Snyder floating ball-type distilling column having three stages. The distillation pot was a 500-ml indented round bottom flask, and the equipment was not insulated. A sample of a bottom fraction was obtained. The bottom fraction contained about 40 weight percent HCC240fa, 40 percent HCC470jfdf plus HCC470nfaf. The balance included tributylphosphate, iron, phosphorous compounds, polymeric material and traces of low boiling chlorinated hydrocarbon compounds.

About 318 grams of this bottom fraction was placed in the flask and heated, while mixing it vigorously with a shaft driven stirrer. Water was fed over a period of about 2.2 hours and three overhead fractions were collected. Thereafter, the water feed was shut off, heating continued for another 0.8 hour while a rather large amount of water present in the pot was driven off.

Taken together, the three overhead fractions contained 93% of the HCC240fa feed from the bottom fraction, and 8.1% of the total HCC470jfdf and HCC470nfaf fed. The cumulative ratio of water overhead to HCC240fa overhead was 13 moles/mole. The cumulative overhead HCC240fa/HCC470nfaf ratio was 19 moles/mole. The first and third overhead aqueous layers were further titrated with sodium hydroxide. They contained less than 19-ppm acid as hydrogen chloride. The low acidity found surprisingly indicates that very low levels of hydrolysis and dehydrochlorination occurred during the steam stripping/separation process.

These results may be compared to the previous results wherein both overhead fractions together contained 98% of the HCC240fa fed, 9% of the two HCC470 isomers fed, and the overhead water/HCC240fa ratio was 11. The cumulative overhead HCC240fa/HCC470nfaf ratio was 17 moles/mole.

The distillation pot, upon cooling, contained two liquid phases, organic and aqueous, with a trace of solids. The solids were easily dislodged from the flask walls upon gently shaking the pot contents. The aqueous phase contained about 10% iron, presumably as ferric chloride.

Example 3

Steam Stripping of Bottom Fraction

The equipment described in Example 2 above, was modified by removing the distillation column and insulating the pot and the overhead take-off adapter. A sample of bottom fraction was obtained. The composition of the bottom fraction and the steam distillation procedure were similar to that described in Example 2.

About 304 grams of the bottom fraction was placed in the flask and heated, while mixing it vigorously with a shaft driven stirrer. A somewhat higher set point was applied to the pot temperature controller during the water addition. The stirrer stopped working for a period of about 0.7 hr, during the 2-hour water addition. Thus, the pot temperature was erratic during that time. Nevertheless, the experiment was successful in preventing a build up of a large water phase in the pot during the distillation, and after the water addition was complete, only 0.1-hour additional heating sufficed to drive off the excess water. The average pot temperature during the water addition was about 111° C., compared to about 106° C. in Example 2.

Two overhead fractions were collected. Together, they contained 93% of the HCC240fa fed, and 1% of the two HCC470 isomers fed. The cumulative overhead water/HCC240fa ratio was 12 moles/mole, almost the same as in Example 2 above. The cumulative overhead HCC240fa/HCC470nfaf ratio was 13 moles/mole.

Compared with the two previous experiments, it appears that relatively more HCC470 isomer was carried out of the pot in this experiment. While not wishing to be bound by any particular theory, it is believed that this might be due to the higher average pot temperature during the current distillation.

Figure 3:
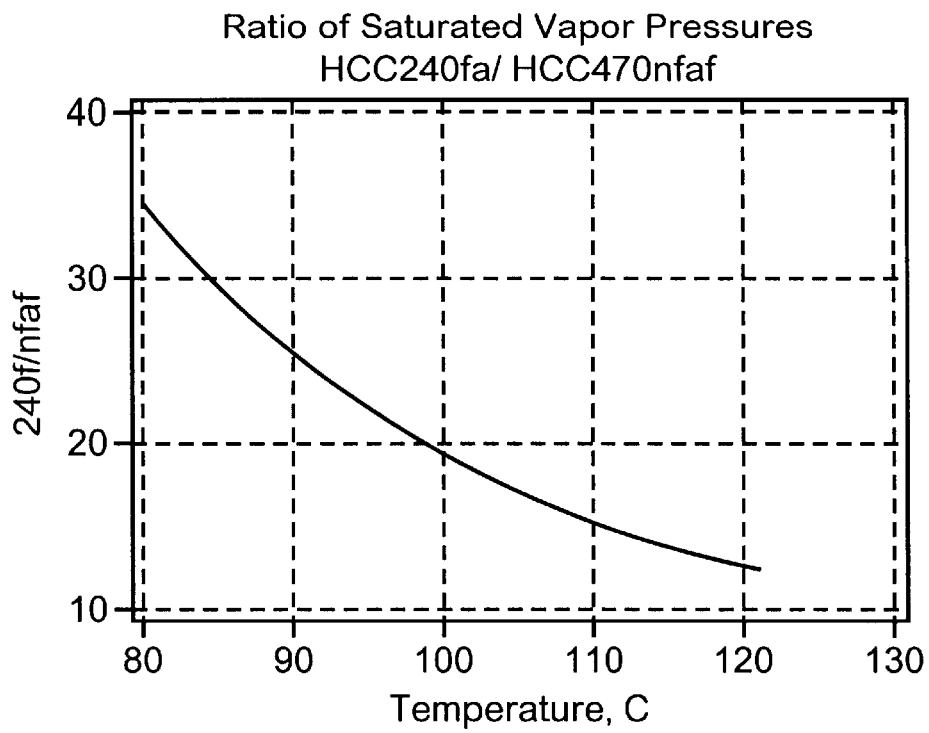
FIG. 3 is a graph illustrating the ratio of the saturated vapor pressures of HCC240fa to that of HCC470nfaf (i.e., the ratio of 1,1,1,3,3-pentachloropropane to 1,1,3,3,5,5-hexachloropentane) as a function of temperature.

FIG. 3, illustrates that the ratio of the saturated vapor pressure of HCC240fa to that of HCC470nfaf decreases with increasing temperature. This ratio, taken together with the liquid concentrations in the pot, should theoretically determine the purity of the HCC240fa overhead.

Figure 4:
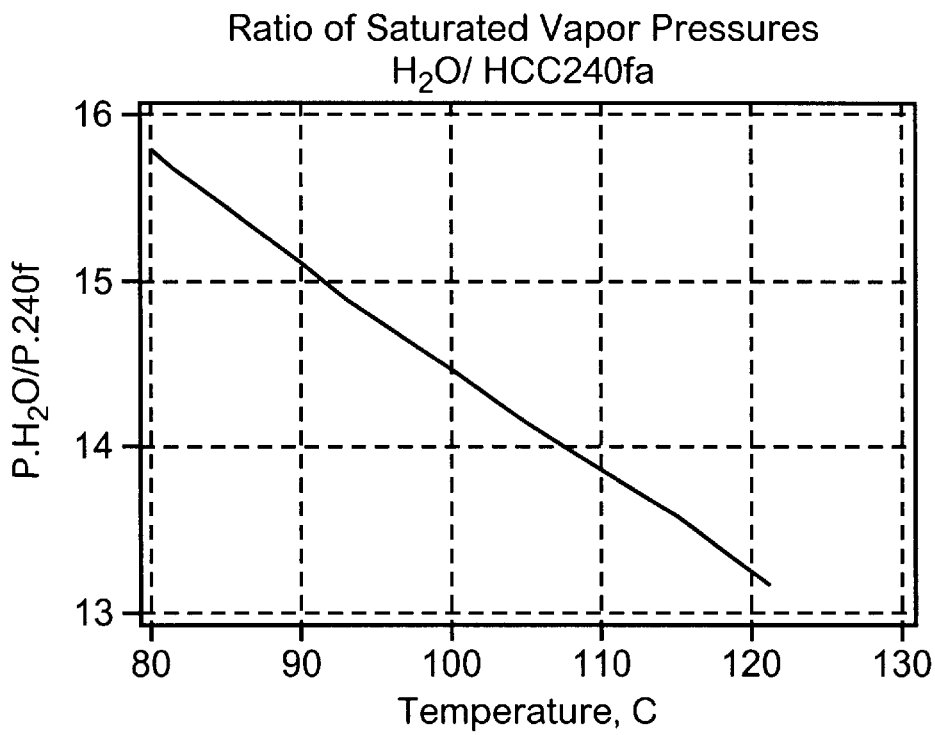
FIG. 4 is a graph illustrating the ratio of the saturated vapor pressure of water to that of HCC240fa (i.e., 1,1,1,3,3-pentachloropropane) as a function of temperature.

Based on the findings in Examples 1–3 it was found that if one wishes to improve the separation between HCC240fa and the HCC470 isomers, one should operate the steam distillation at lower pot temperatures, such as by operating at reduced pressure. However, the ratio of the saturated vapor pressure of water to that of HCC240fa increases with decreasing temperature. See, FIG. 4. Thus, more water per pound of HCC240fa stripped would be needed to operate at a lower temperature.

Upon review of the results, it can be seen that HCC240fa halogenated alkane (1,1,1,3,3-pentachloropropane) was surprisingly separated from the heavy ends in a fast and facile manner. Moreover, the halogenated alkane recovered was significant.

While the invention has been described in detail with reference to specific embodiments thereof, it will be apparent to those skilled in the art that various changes and modifications can be made, and equivalents employed, without departing from the scope of the claims which follow.

What is claimed is:

1. A method for the separation of heavy ends from a halogenated alkane stream, comprising:
    (a) removing a bottom fraction containing heavy ends from a catalyst recovery unit and conveying said bottom fraction to a vessel;
    (b) introducing steam into said bottom fraction containing heavy ends;
    (c) removing halogenated alkane vapor and water vapor from said treatment unit;
    (d) condensing said halogenated alkane and water vapors;
    (e) separating the halogenated alkane phase from the water phase; and
    (f) purging the heavy ends, which remain in the treatment unit either periodically or continuously.

2. The method for the separation of heavy ends in accordance with claim 1, further comprising:
    drying the halogenated alkane phase.

3. The method for separation of heavy ends in accordance with claim 2, further comprising:
    processing the halogenated alkane to manufacture a purified product.

4. The method for the separation of heavy ends in accordance with claim 1, further comprising:
    converting said water phase into steam and reusing said steam to treat a further bottom fraction containing heavy ends.

5. The method for the separation of heavy ends in accordance with claim 1, further comprising:
    removing said bottom fraction containing heavy ends from said catalyst recovery unit and conveying a part of said bottom fraction to said vessel.

6. The method for the separation of heavy ends in accordance with claim 1, wherein said heavy ends is a mixture containing catalyst, solvent, metal particles, metal chlorides and high boiling chlorinated by-products.

7. A method for the separation of heavy ends from a halogenated alkane stream, comprising:
    (a) removing a bottom fraction containing heavy ends from a catalyst recovering unit and conveying said bottom fraction to a vessel;
    (b) maintaining the temperature of said vessel above the boiling point of water at a predetermined pressure;
    (c) introducing water into said vessel where a portion of the water is converted into steam and is mixed with said heavy ends and a portion of unconverted water fluid to form a haloalkane vapor, and removing a portion of the vapors from the vessel;
    (d) condensing said haloalkane mixture and the remaining portion of steam; and
    (e) separating a halogenated alkane phase from the water recovered.

8. The method for the separation of heavy ends from a halogenated alkane stream in accordance with claim 7, further comprising:
    passing said haloalkane vapor and steam from step (c) through a column to further fractionate the mixture.

9. The method for the separation of heavy ends from a halogenated alkane stream in accordance with claim 7, wherein step (b) is carried out by:
    operating said vessel at a pressure in the range of about 0.1 to 5.0 atmospheres.

10. The method for the separation of heavy ends from a halogenated alkane stream in accordance with claim 7, wherein step (b) is carried out by:
    operating said vessel at a pressure in the range of about 0.5 to 1.5 atmospheres.

11. The method for the separation of heavy ends from a halogenated alkane stream in accordance with claim 7, wherein step (b) is carried out by:
    operating said vessel at a temperature range of about 40 to 150° C.

12. The method for the separation of heavy ends from a halogenated alkane stream in accordance with claim 7, wherein step (b) is carried out by:
    operating said vessel at a temperature range of about 40 to 115° C.

13. The method for the separation of heavy ends from a halogenated alkane stream in accordance with claim 7, further comprising:
    treating said water which has been recovered to remove or to neutralize any acidity present.

14. The method for the separation of heavy ends from a halogenated alkane stream in accordance with claim 7, further comprising:
    recycling the water which has been recovered to treat a further halogenated.

15. The method for the separation of heavy ends from a halogenated alkane stream in accordance with claim 7, wherein
    said halogenated alkane phase is further treated to manufacture a purified product.

* * * * *